United States Patent [19]

Schuss et al.

[11] 4,332,562
[45] Jun. 1, 1982

[54] DENTAL HANDPIECE

[75] Inventors: Werner Schuss, Heppenheim; Ernst-Otto Fleer, Bensheim, both of Fed. Rep. of Germany

[73] Assignee: Siemens Aktiengesellschaft, Berlin & Munich, Fed. Rep. of Germany

[21] Appl. No.: 202,137

[22] Filed: Oct. 30, 1980

[30] Foreign Application Priority Data

Nov. 29, 1979 [EP] European Pat. Off. ........... 79104765

[51] Int. Cl.$^3$ ............................................... A61C 1/08
[52] U.S. Cl. ...................................................... 433/126
[58] Field of Search ................................ 433/126, 105

[56] References Cited

U.S. PATENT DOCUMENTS

| 1,355,659 | 10/1970 | Evslin .................................. 433/126 |
| 3,229,369 | 1/1966 | Hoffmeister et al. |
| 4,255,143 | 3/1981 | Schuss et al. ....................... 433/126 |

*Primary Examiner*—Robert Peshock
*Attorney, Agent, or Firm*—Hill, Van Santen, Steadman, Chiara & Simpson

[57] ABSTRACT

A dental handpiece which has at least two handpiece parts each having a drive shaft and a cooling line segment for at least one cooling line agent and an arrangement for releasably interconnecting the two parts with the gears of the drive shaft in driving engagement, the connecting arrangement including a guide fitting strip arranged on one of the handpiece parts and extending axially therefrom to be engaged in an axial extending guide slot in the other handpiece part to prevent twisting between the connected parts, characterized by the connecting arrangement comprising at least one catch element provided on one handpiece part and coacting with a counter element on the other handpiece part, and each of the cooling line segments of the one handpiece part extending into the guide fitting strip, the other handpiece part having a portion supporting each of its cooling line segments to project from a surface into the guide slot to form an axial connection with the segments of the fitting strip and a sealing arrangement for sealing each of the axial connection being formed.

11 Claims, 8 Drawing Figures

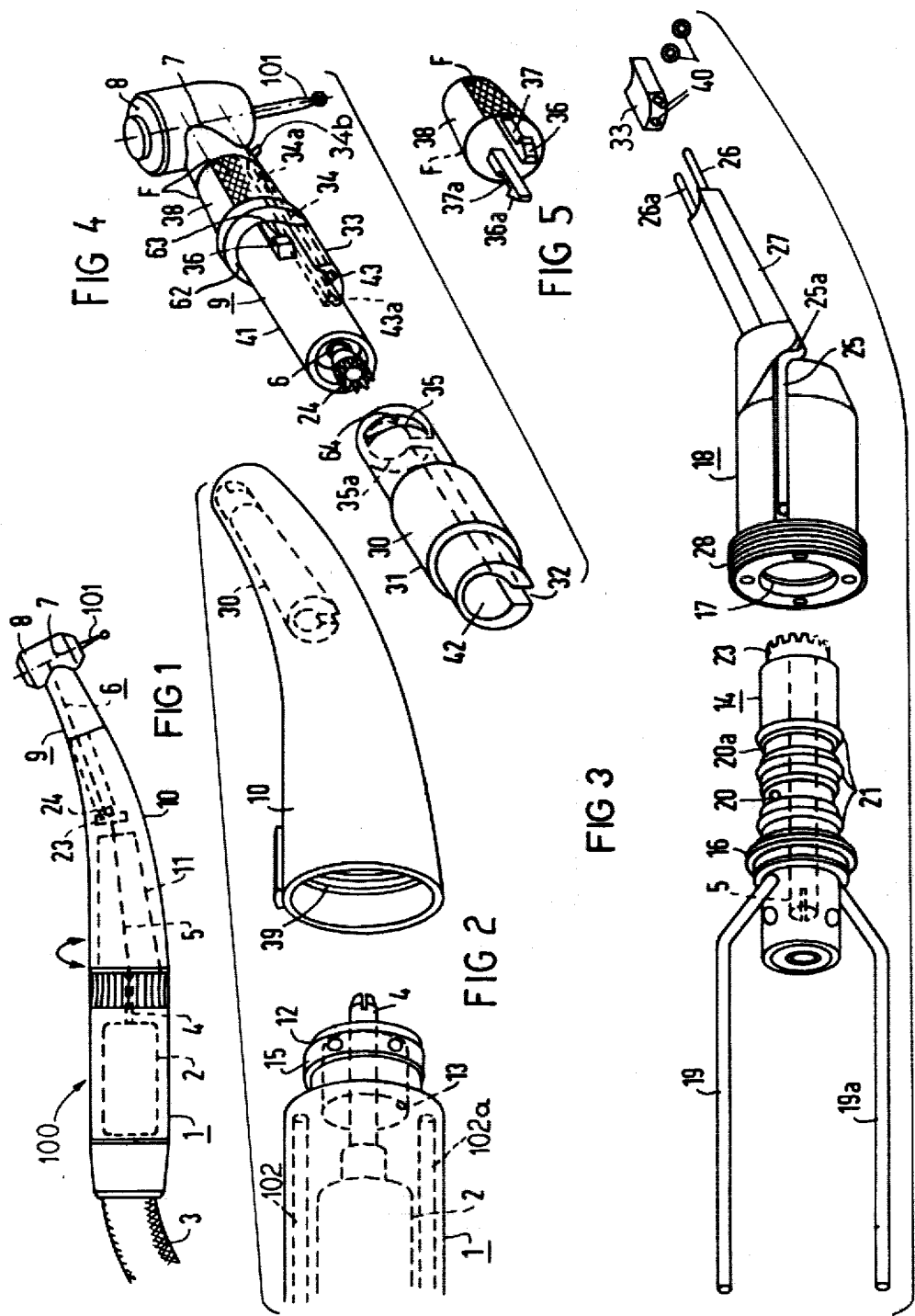

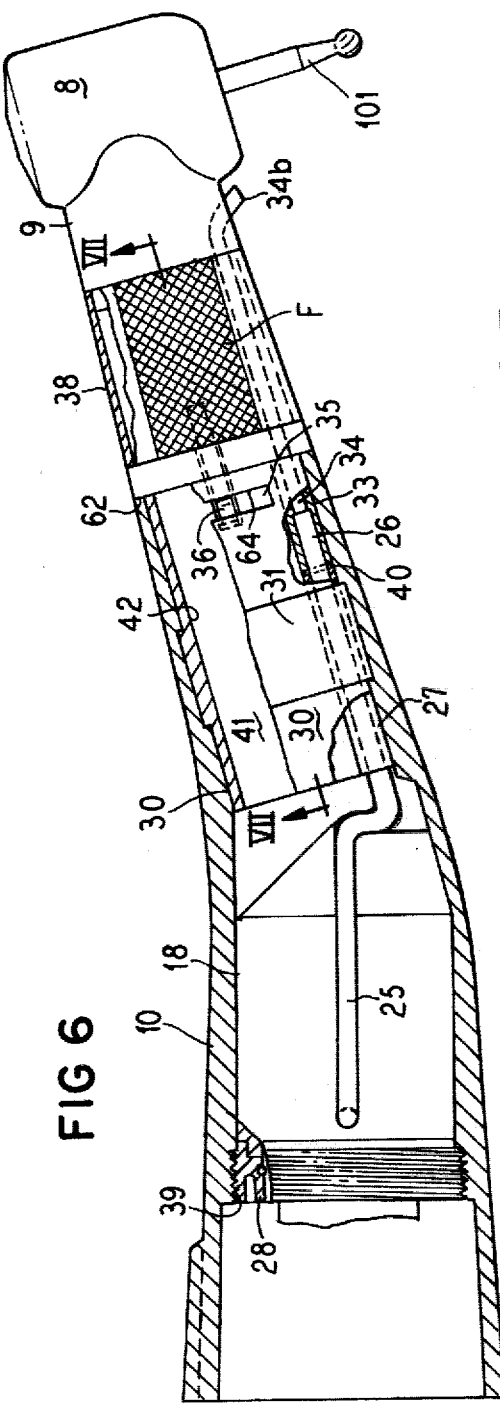
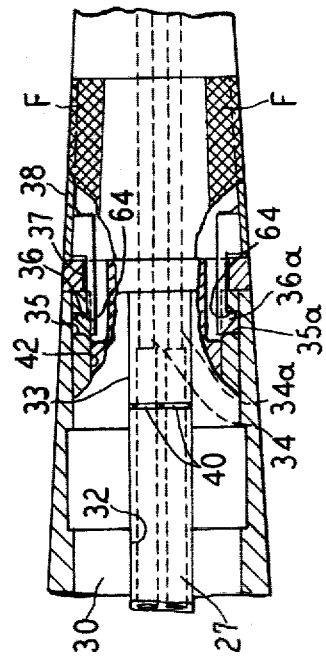
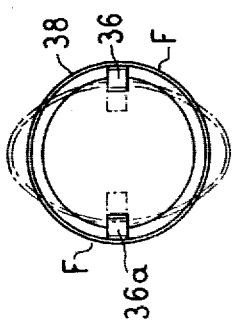

DENTAL HANDPIECE

BACKGROUND OF THE INVENTION

The present invention is directed to a dental handpiece which has at least two handpiece parts, each having a drive shaft and a cooling line segment for at least one cooling agent, connecting means for releasably interconnecting the two parts with gears of the drive shafts in driving engagement enabling said connecting means including means for preventing relative twisting between the two handpiece parts including a guide fitting strip arranged on one of the handpiece parts and extending axially therefrom to be engaged in an axially extending guide slot in the other handpiece part.

For the axial connection of two handpiece parts, it is known to align these parts in their desired angular position with respect to one another with the assistance of a pin engaged in a longitudinal slot or bore and to then connect the two handpiece parts to one another by means of a coupling sleeve. In this construction, the cooling agent line sections or segments are formed by means of exposed hoses which are arranged along the outside of the handpiece parts. This type of connection involves too much time for a quick interchange of handpiece parts.

Another type of dental handpiece construction is disclosed in German O.S. No. 2,802,325. In this device, the connecting means contains the slotted sleeve and a recess arranged diametrically offset with respect thereto on the circumference of the one handpiece part. The other handpiece part has projections fitting into the slot. The sleeve and the mandrel exhibit elastic deformable parts, which after axial insertion of the mandrel into the sleeve slot allow the mandrel projections to engage in the sleeve recess and hold it locked therein after subsequent twisting of the two handpiece parts along the longitudinal axis. The connection and sealing of the two coolant line ends at the coupling location are obtained via a ring seal between the abutting end faces of the two handpiece parts. The height or the axial length of the ring seals is somewhat greater than the axial depth of the bore in which the ring seal is inserted so that the ring seal projects slightly above the one end face in the uncoupled state and a surface seal with a specific surface pressure is achieved in the coupled state.

So that a tight connection of the cooling agent line sections is guaranteed, a relatively great surface pressure must be generated which in the final analysis leads to the bayonet type connection of the two handpiece parts to be relatively tight. Since the seal is loaded for shearing or respectively torsion at practically every coupling and uncoupling operation, relatively high wear of this seal will occur with this type of structure.

For solving the problems of conveying a cooling line agent between two handpiece parts, it is also known to secure to the one handpiece part a cooling agent line section in the form of a rigid tube with an excessive length corresponding approximately to the length of the other handpiece part. When the other handpiece part is removed, the cooling agent line section allocated to the other handpiece part remains on the one handpiece part and projects therefrom. Given such an arrangement however, there is a danger that the relatively thin cooling agent lines will be bent or damaged in some other manner and that exact recoupling is thus no longer guaranteed.

SUMMARY OF THE INVENTION

The present invention is directed to creating a solution which is an improvement over the previous devices, is simpler to to manipulate and exhibits a lower wear of the parts. In particular, the present invention provides a solution which requires only a light exertion of force in order to couple or uncouple the two handpiece parts but which nonetheless guarantees the secure coupling with a tight connection of the cooling agent line sections or segments.

In order to achieve the present object, the present invention is directed to an improvement in a dental handpiece having at least two handpiece parts, each of said handpiece parts having a drive shaft and a cooling segment or section for at least one cooling agent, connecting means for releasably interconnecting the two parts with the gears of the drive shaft in driving engagement, said connecting means including means for preventing relative twisting between the two handpiece parts, said means for preventing including a guide fitting strip arranged on one of said handpiece parts and extending axially therefrom to be engaged in an axially extending guide slot in the other handpiece part. The improvement comprises said means for connecting comprising at least one catch element provided on the one handpiece part coacting with a counter element arranged on the other handpiece part, said catch element and counter element being disengageable to enable disassembly of said connecting means and each of the cooling line segments in the one handpiece part extending into the guide fitting strip, the other handpiece part having a portion supporting each of its cooling line segments projecting from a surface into the guide slot to form an axial connection with the segments of the fitting strip and means for sealing being provided so that during connection of the two parts, an axial connection sealed by the sealing means is formed.

A significant advantage of the inventive construction is that the two handpiece parts for coupling and uncoupling cannot be twisted with respect to one another but on the contrary are axially removed and/or assembled with each other. Thus, the connection of the cooling agent lines of the two handpiece parts are produced and/or released at the same time as the assembly and disassembly of the two parts. Particular advantages result in the employment of the connection for the coupling and uncoupling of the head part to the grip sleeve portion of the dental handpiece because the coupling and uncoupling operation must be carried out relatively frequently.

BRIEF DESCRIPTION OF THE DRAWINGS

FIG. 1 is a side view of a dental handpiece in accordance with the present invention;

FIG. 2 is a partial exploded perspective view of the dental handpiece of FIG. 1;

FIG. 3 is a partial exploded perspective of internal parts of the dental handpiece of FIG. 1;

FIG. 4 is another partial exploded view of the head portion and internal parts of the handpiece;

FIG. 5 is a perspective view of a portion of the headpiece illustrated in FIG. 4;

FIG. 6 is a longitudinal cross-sectional view with portions in elevation of the sleeve part and head part assembled together;

FIG. 7 is a partial cross-sectional view with portions in elevation taken generally along line VII—VII in FIG. 6; and FIG. 8 is an end view of the sleeve of FIG. 5 with the released position illustrated in broken lines.

DESCRIPTION OF THE PREFERRED EMBODIMENTS

The principles of the present invention are particularly useful in a dental handpiece generally indicated at 100 in FIG. 1.

The handpiece 100 is composed of a drive section or part 1, an angled portion or sleeve part 10 and a head part or portion 9. The drive section or part 1 contains a drive motor 2 for example an electric motor 2, which receives its drive energy by a supply hose 3 and has a drive shaft 4. In the angled portion 10, a drive train composed of drive shafts 5 and 6 transfer rotational motion or output from the drive shaft 4 to a rotatable tool acceptance shaft or socket 7 that receives and supports a dental tool such as a drill 101 for rotation in a head housing 8 of the head part 9. The head housing 8 is part of the head part which accepts the two drive shaft sections 6 and 7 as well as their bearings and which is removably seated on a handpiece gripping sleeve which is an angled portion 10. The sleeve part 10 encloses a bearing unit 11 which is formed of two concentric sleeves or sleeve elements 14 and 18 (FIG. 3) that have bearing units for the drive shaft section 5 as well as the rotational connection for conveying one or more cooling agents from the drive part or section 1 to the head part or section 9. The handpiece gripping sleeve 10 together with the head part 9 and the bearing unit 11, which will be described in greater detail below, will rotate with respect to the drive part 1 around the longitudinal axis of the handpiece which is the axis of the drive shaft 4.

The drive part 1 (FIG. 2) has a sleeve-like or cylindrical shoulder 12 surrounding a socket 13 indicated in broken lines through which the drive shaft 4 extends. The socket 13 receives one end of the sleeve 14 when the handpiece parts are assembled. On an outer surface of the shoulder or sleeve 12, a ball catch 15 is provided for axially securing the sleeve 14 in the socket 13. The sleeve 14, which is best illustrated in FIG. 3, contains a spring washer 16 which is received in a snap ring groove 17 of the sleeve element 18 during assembly and the assembled sleeves 14 and 18 form the bearing unit 11. Two cooling agent lines 19 and 19a are secured to the sleeve 14 and the ends of the cooling lines discharged in a known manner via radial bores or ports into annular channels 20 and 20a, which are sealed from one another by means of packing rings such as O-rings 21. In addition, the sleeve 14 also accepts and supports the first drive shaft 5 which has one end connected to the drive shaft 4 of the motor 2 and the opposite end supporting a bell-shaped drive gear 23 which will be engaged with a gear 24 (FIG. 4) on the drive shaft section 6. In the assembled state, the ends of the cooling lines sections 19 and 19a will project from the sleeve 14 and are engaged in longitudinal grooves and/or bores 102, 102a of a drive housing of the drive part 1 and can be connected to a supply lines which are conveyed in the hose 3.

In an assembled state, sleeve 18 (FIG. 3) is arranged concentric to the sleeve 14 and contains the cooling line sections 25 and 25a which in turn accept the cooling agent from the annular grooves 20 and 20a in a known manner. The cooling lines 25 and 25a terminate in tubular prongs 26 and 26a which are mounted in a diagonally extending portion or extension 27 of the sleeve 18. The sleeve 18 further contains a threaded ring 28, which is rotatably mounted on the sleeve 18 without axial displacement and contains a snap ring groove 17 for engagement with the spring washer 16 when the sleeve 18 is assembled on the sleeve 14. The sleeve 18 is axially secured in the handpiece by means of the threaded ring 28 being threaded into threads 39 (FIG. 2) of the sleeve of the grip portion 10.

The grip portion or part 10 as illustrated in FIG. 2, adjacent the head 9 receives a resilient, slotted guide bushing or grasping sleeve 30. As best illustrated in FIG. 4, the bushing 30 has a collar 31 which is snapped into a socket of the sleeve part 10. The guide bushing 30 is thus secured in the handpiece part 10 against axial slippage. As illustrated, the guide bushing 30 is provided with a cylindrical bore 42 and a continuous longitudinal slot 32 which receives the projecting portion or extension 27 of the sleeve 18 and also a longitudinal fitting strip or member 33 of the head part 9. As illustrated, the strip 33 of the head part 9 contains cooling agent line sections 34 and 34a which discharge into a common cooling agent discharge nozzle 34b in the area of the tools supported in the head 8.

The guide bushing 30 serves to prevent twisting of the part 18 relative to the part 9 and also contains two circumferentially spaced catch slots 35 and 35a which are shown as being on both sides of the bushing. The slots 35 and 35a receive radial resilient catch noses 36 and 36a when the head part 9 is axially assembled onto the grip section or portion 10. The two catch noses 36 and 36a are secured on a spring-like tubular sleeve or member 38 (FIG. 5) by means of bridges 37 and 37a which extend parallel to the axis of the sleeve. The spring sleeve or resilient member 38 is designed with a very thin wall and is arranged on the head part 9 in such a manner that it forms an outer generated surface. By means of radial pressure against the sleeve 38 for example by using the thumb and index finger, the two catch noses 36 and 36a can be moved radially towards the inside (see FIG. 8) and therefore will be released or disengaged from the slots 35 and 35a.

The bridges 37 need not be absolutely rigidly arranged on the actuation sleeve 38. It is also conceivable within the framework of the invention for the catch nose 36 instead of extending radially outward as illustrated to be arranged to extend radially inward. Variations of the sample embodiment illustrated are also possible with respect to the number of catch noses provided without leaving the framework of the invention. The disposition of the two catch noses lying diametrically opposite one another, however, is particularly advantageous although it is also conceivable to provide only one catch nose or three or respectively four catch noses for specific purposes. An embodiment in which the resilient sleeve is provided with one or more recesses on a circumference and the bridges together with the catch noses are arranged on the member 30 is also within the framework of the present invention.

For assemblying the handpiece, the bushing 30 is first clamped into the sleeve part 10. The collar 31 is thus engaged in the corresponding socket of a sleeve part 10 and prevents axial dislocation of the bushing. Subsequently, the sleeve 18 is inserted into the handpiece portion 10 with the extension 27 engaged in the longitudinal slot 32 of the guide bushing 30. By means of the threaded ring 28, which is rotatably mounted on the sleeve 18, the sleeve 18 is axially fixed within the handpiece portion 10 as the threads of the ring 28 are received in the internal threads 39.

The sleeve 14 as already mentioned is connected in a twist proof but axially releasable manner on the drive part 1 by means of the ball catch device 15. The handpiece grip or sleeve portion 10 with the guide bushing 30 supported therein and the sleeve 18 with the cooling agent lines 25 and 25a can now be axially slipped onto the sleeve 14 until the spring washer 16 is received by the groove 17 and the two handpiece parts are then axially fixed or connected together.

The head part 9 in addition to including the spring-like sleeve 38 has a tubular shank or neck part 41 with a portion of the fitting strip 33 extending from one side thereof. When the head part 9 is assembled with the grip portion 10, the shank 41 is received in the bore 42 of the bushing 30 and the strip 33 is received in a portion of the slot 32. Thus, the head part 9 will be secured against twisting relative to the bushing 30 and to the sleeve 18. Prior to assembly, elastic seals 40 consisting of one or more elements are inserted over the prong-like projections 26 and 26a of the coolant lines 25 and 25a. Thus, during assembly the prongs 26 and 26a will be received in sockets 43 and 43a of the member 33 to complete the axial connection to the cooling agent line sections 34 and 34a. The amount of insertion of the shank into the bore 42 is limited by a shoulder 62 but not until after the catch noses 36 and 36a have been engaged in the catch slots 35 and 35a so that the head part 9 is first axially fixed with respect to the grip sleeves or portion 10. In the catch position, the seals guarantee a tight connection between the cooling line sections 25 and 34.

In addition, the seals 40 also fulfill another function namely providing sufficient clearance between the two gears 23 and 24 for proper meshing engagement. To this end, the two catch noses 36 and 36a are engaged in the slots 35 and 35a with a slight axial play. The pre-stress force created by the seals 40 will bias the head part 9 away from the grip sleeve 10. Thus, the desired clearance between the handpiece parts in the axial direction is obtained due to the detent of the engagement surface or edge 63 of the catch nose 36 and 36a being engaged tightly against the engagement surfaces or sides 64 of the slot such as 35 and 35a. Due to this arrangement, the shoulder 62 can be eliminated.

Instead of utilizing the elastic seals 40, a spring wire, a spring band or the like can be inserted at right angles to the cooling fluid line sections 34. These spring members can be provided to act on an end face of the fitting strip or member 33 or a part thereof to bias and urge the head part 9 away from the sleeve part 10. This biasing ensures the axially effective pressure and spacing between the two gears 23 and 24 when the handpiece parts are properly connected.

For releasing the head part 9, the spring sleeve 38 is pressed slightly together in a radial direction in the surface area F which are a knurled outer portion adjacent each of the catch noses 36 and 36a. By means of this pressing together, which is expediently accomplished by the thumb and index finger, the spring sleeve is deformed thereby moving the catch nose from an engagement in the respective slots. The arrangement of the catch connection in the area illustrated allows a safe connection and disconnection of the handpiece parts because the head part need be grasped particularly only at the side surfaces, which is the surface area which merges tangently into the head housing 8.

Although various minor modifications may be suggested by those versed in the art, it should be understood that we wish to embody within the scope of the patent granted hereon, all such modifications as reasonably and properly come within the scope of our contribution to the art.

We claim:

1. A dental handpiece comprising at least a first handpiece part; a second handpiece part, each of said handpiece parts having a drive shaft with a gear at each end and a cooling line segment for at least one cooling agent; and connecting means for releasably interconnecting the handpiece parts together with the gears of the drive shafts in driving engagement, said connecting means including means for preventing relative twisting between the handpiece parts and at least one catch element being provided on the first handpiece part co-acting with a counter element arranged on the second handpiece part, said catch element and counter element being disengageable to enable disassembly of the connecting means, said means for preventing including a guide member arranged on one of said first and second handpiece parts and extending axially therefrom to be engaged in an axially extending guide slot in the other of said first and second handpiece parts, said guide member supporting the cooling line segment of the one handpiece part with each segment opening on a surface of said guide member, the other handpiece part having a portion supporting each of its cooling line segments with the segments projecting from a surface of the portion into the guide slot and into said openings to form an axial connection with the segments of the guide member, and said connecting means including means for sealing the axial connection of the segments so that during connection of the two parts together, a sealed axial connection of the segments of the parts is formed.

2. A dental handpiece according to claim 1, wherein each of the catch elements has an engagement surface for contacting an engagement surface of the counter element when the connection is formed, said connecting means including elastic pressure means being disposed between the handpiece parts for biasing the engagement surface of each catch element against its respective engagement surface of the counter element so that an exact spacing between the two engaged gears carried by the drive shaft of said parts is obtained.

3. A dental handpiece according to claim 2, wherein said elastic pressure means for biasing comprises the means for sealing.

4. A dental handpiece according to claim 2, wherein the means for biasing comprises a resilient member extending between the end of the guide member and a surface of said portion of the other handpiece part to bias the two parts axially apart.

5. A dental handpiece according to claim 1, wherein the other handpiece has a guide bushing having the guide slot, said guide slot receiving an extension forming the portion with the cooling segments of the other part and said segments projecting from a surface of said extension, said one handpiece part having a shank portion with the guide member extending from a side thereof, said shank portion being received in said guide bushing with the guide member received in said slot.

6. A dental handpiece according to claim 5, wherein the guide member has a slight taper extending towards its free end and a portion of the guide slot receiving the guide member having a corresponding expanding taper.

7. A dental handpiece according to claim 1, wherein the connecting means includes a resilient sleeve member disposed on the one handpiece part, each of said catch elements being formed on an end of a bridge member secured to the sleeve member to extend substantially along the axial direction thereof, each of said counter elements being a recess provided in the other handpiece part so that the catch element is automatically engaged in the recess during axial assembly of the two handpiece parts.

8. A dental handpiece according to claim 7, wherein each recess is provided on a guide bushing having the guide slot.

9. A dental handpiece according to claim 1, wherein the one handpiece part is a head part having a drive shaft for rotating a socket which supports a tool for rotation, the other handpiece part comprises a sleeve part containing at least one drive shaft section, said head part having a shank portion with the guide member extending from a side thereof and said connecting means including a resilient sleeve-like member telescopically received on said shank portion and operately connected to each catch element, said sleeve part of the other handpiece part containing a guide bushing having a longitudinally extending guide slot for receiving the guide member during assembly of said parts, each counter element of the connecting means being formed by a recess provided in the end of the guide bushing.

10. A dental handpiece according to claim 9, wherein the guide bushing is a radially resilient bushing having a collar on an exterior surface thereof, said sleeve part having a socket for receiving said guide bushing and said collar under radial prestressed conditions and preventing axial displacement of said bushing.

11. A dental handpiece according to claim 9, wherein the sleeve part has a sleeve-shaped element received in an outer sleeve-shaped member, said sleeve-shaped element having an extension received in said guide slot to prevent twisting therebetween, said extension being the portion supporting the cooling line segments with portions extending from the end surface thereof.

* * * * *